(12) United States Patent
Murugan

(10) Patent No.: US 9,193,683 B2
(45) Date of Patent: Nov. 24, 2015

(54) PROCESS FOR PREPARING DIHALOPYRIDINES

(71) Applicant: VERTELLUS SPECIALTIES INC., Indianapolis, IN (US)

(72) Inventor: Ramiah Murugan, Indianapolis, IN (US)

(73) Assignee: Vertellus Specialties Inc., Indianapolis, IN (US)

( * ) Notice: Subject to any disclaimer, the term of this patent is extended or adjusted under 35 U.S.C. 154(b) by 0 days.

(21) Appl. No.: 14/404,819

(22) PCT Filed: May 31, 2013

(86) PCT No.: PCT/US2013/043703
§ 371 (c)(1),
(2) Date: Dec. 1, 2014

(87) PCT Pub. No.: WO2013/181592
PCT Pub. Date: Dec. 5, 2013

(65) Prior Publication Data
US 2015/0152055 A1    Jun. 4, 2015

Related U.S. Application Data

(60) Provisional application No. 61/654,153, filed on Jun. 1, 2012.

(51) Int. Cl.
C07D 211/72 (2006.01)
C07D 213/04 (2006.01)
C07D 213/61 (2006.01)
C07D 213/73 (2006.01)

(52) U.S. Cl.
CPC ............ *C07D 213/04* (2013.01); *C07D 213/61* (2013.01); *C07D 213/73* (2013.01)

(58) Field of Classification Search
None
See application file for complete search history.

(56) References Cited

U.S. PATENT DOCUMENTS

| | | |
|---|---|---|
| 5,380,274 A | 1/1995 | Nita |
| 2007/0161797 A1 | 7/2007 | Shapiro |
| 2010/0160641 A1* | 6/2010 | Modi et al. ..................... 546/345 |
| 2010/0301255 A1 | 12/2010 | Eskilsson et al. |

OTHER PUBLICATIONS

PCT Search Report and Written Opinion for PCT/US2013/043703, completed Dec. 10, 2013.
Hodgson, Herbert H., "The Sandmeyer Reaction", 1947, Chemical Reviews No. 40(2), pp. 251-277.

* cited by examiner

*Primary Examiner* — Heidi Reese
(74) *Attorney, Agent, or Firm* — Barnes & Thornburg LLP

(57) ABSTRACT

Processes for manufacturing dihalopyridines without the use of copper salts are described. Additional processes for manufacturing dihalopyridines from niacinamide are described.

22 Claims, No Drawings

PROCESS FOR PREPARING DIHALOPYRIDINES

CROSS-REFERENCE TO RELATED APPLICATIONS

This application is a national stage entry under 35 USC §371(b) of International Application No. PCT/US2013/043703, filed May 31, 2013, which claims priority under 35 U.S.C. §119(e) to U.S. Provisional Application No. 61/654,153, entitled "Process For Preparing Dihalopyridines," filed Jun. 1, 2012. The entirety of the disclosures of these applications are incorporated herein by reference.

TECHNICAL FIELD

The invention described herein pertains to processes for the manufacture of dihalopyridines.

BACKGROUND AND SUMMARY

Dihalopyridines comprise an important group of compounds useful as intermediates in the manufacture of several commercial materials. For example, 2,3-dichloropyridine is an important raw material for the preparation of crop protection agents, pharmaceuticals and other fine chemicals. A need exists for efficient and practical processes for the manufacture of 2,3-dichloropyridine that are environmentally benign.

2,3-Dichloropyridine has been made from 5,6-dichloronicotinic acid by decarboxylation and from 3-amino-2-chloropyridine by diazotization/chlorination. The manufacture of 2,3-dichloropyridine from 3-amino-2-chloropyridine using a modified Sandmeyer reaction approach has also been reported. The Sandmeyer reaction generally requires preparation of a diazonium salt from 3-amino-2-chloropyridine with an alkali nitrite followed by reaction in the presence of a copper(I) or copper(II) salt. Stoichiometric amounts of the copper salts are typically used to provide efficient preparation of the dichloropyridine from the diazonium salt, resulting in the need for costly recovery of expensive and potentially toxic copper by-products from the process waste stream. Additionally, isolation of the 2,3-dichloropyridine is usually accomplished by extraction of the 2,3-dichloropyridine from the reaction mixture with a water immiscible solvent followed by removal of the solvent adding to the amount of waste that must be processed.

A process for the preparation of 2,3-dibromopyridine involving temperature dependent displacement of chloride by bromide during the diazotization of 3-amino-2-chloropyridine, followed by addition of CuBr in 48% HBr resulting in high yields of 2,3-dibromopyridine has been previously disclosed.

Although diazonium salts are usually prepared in a separate step and subsequently added to a mixture containing the copper salt, requiring the accumulation of potentially hazardous amounts of the unstable diazonium salt, the addition of sodium nitrite to a solution of 3-amino-2-chloropyridine containing copper salts leading to 2,3-dichloropyridine has been disclosed.

Several processes for providing the starting material for the Sandmeyer reaction, e.g. 3-amino-2-chloropyridine, have been previously disclosed, including chlorination of 3-amino-pyridine using chlorine or hydrogen peroxide and hydrogen chloride. Formation of 3-amino-pyridine from niacinamide has also been previously disclosed.

A process for the manufacture of dihalopyridines has been discovered that does not require the use of expensive and potentially environmentally harmful copper salts, does not require the use of multiple reaction vessels, and does not require the use of additional solvents for isolation of the dihalopyridine.

In one embodiment of the invention, a process is described for the manufacture of a compound of formula (A)

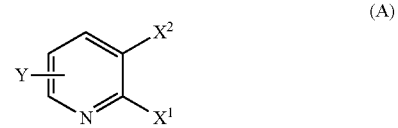

wherein $X^1$ and $X^2$ are in each instance independently selected from the group consisting of Cl and Br;

Y represents from 0 to 3 substituents independently selected in each instance from the group consisting of halide, CN, $NO_2$, OH, optionally substituted alkyl, optionally substituted aryl, and optionally substituted heteroaryl; and wherein the process comprises the step of adding a first liquid mixture comprising a metal nitrite salt to a second liquid mixture comprising a compound of formula (B)

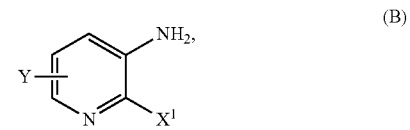

a hydrohalic acid, and an iron(III) compound.

DETAILED DESCRIPTION

Several embodiments of the invention are described by the following enumerated clauses:

1. A process for the manufacture of a compound of formula (A)

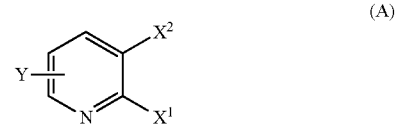

wherein $X^1$ and $X^2$ are in each instance independently selected from the group consisting of Cl and Br;

Y represents from 0 to 3 substituents independently selected in each instance from the group consisting of halide, CN, $NO_2$, OH, optionally substituted alkyl, optionally substituted aryl, and optionally substituted heteroaryl; and wherein the process comprises the step (c) of adding a first liquid mixture comprising a metal nitrite salt to a second liquid mixture comprising a compound of formula (B)

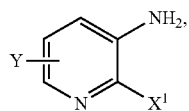

a hydrohalic acid, and an iron(III) compound.

1a. A process for the manufacture of a compound of formula (A)

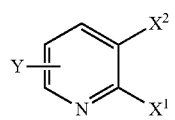

wherein $X^1$ and $X^2$ are in each instance independently selected from the group consisting of Cl and Br;

Y represents from 0 to 3 substituents independently selected in each instance from the group consisting of halide, CN, $NO_2$, OH, optionally substituted alkyl, optionally substituted aryl, and optionally substituted heteroaryl; and wherein the process comprises the step (c) of adding a first liquid mixture comprising a metal nitrite salt to a second liquid mixture comprising a compound of formula (B)

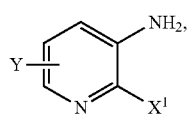

a hydrohalic acid, and an iron salt.

2. The process of any one of the preceding clauses further comprising the step (b) of reacting a compound of formula (C)

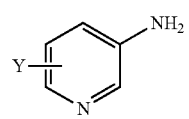

with a first halogenating agent in the presence a hydrohalic acid to give the compound of formula (B).

3. The process of any one of the preceding clauses further comprising the step (a) of reacting a compound of formula (D)

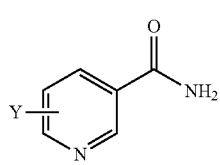

with a base and a second halogenating agent to give the compound of formula (C).

4. The process of clause 2 wherein steps (b) and (c) are conducted in the same reaction vessel.

5. The process of clause 3 wherein steps (a), (b), and (c) are conducted in the same reaction vessel.

6. The process of clause 3 wherein the second halogenating agent is selected from the group consisting of group consisting of chlorine, N-chlorosuccinimide, bromine, N-bromosuccinimide, hypochlorous acid, hypobromous acid, alkali metal hypochlorites, alkali metal hypobromites, and benzyltrimethyl ammonium tribromide.

6a. The process of any one of the preceding clauses wherein the first halogenating agent is selected from the group consisting of bromine, N-bromosuccinimide, chlorine, N-chlorosuccinimide, hydrochloric acid and hydrogen peroxide, hypochlorous acid, hypobromous acid, alkali metal hypochlorites, alkali metal hypobromites, and benzyltrimethyl ammonium tribromide.

7. The process of any one of the preceding clauses wherein Y is not present.

8. The process of any one of the preceding clauses wherein $X^1$ is chloro.

9. The process of any one of the preceding clauses wherein $X^2$ is chloro.

9a. The process of any one of the preceding clauses wherein Y is absent; and $X^1$ and $X^2$ are both chloro.

10a. The process of any one of the preceding clauses wherein the iron salt is selected from the group consisting of ferric chloride, ferric nitrate, ferric sulfate, ferrous chloride, ferrous nitrate, and ferrous sulfate.

10b. The process of any one of the preceding clauses wherein the iron salt is ferric chloride.

10c. The process of any one of the preceding clauses wherein the hydrohalic acid is hydrochloric acid.

10d. The process of any one of the preceding clauses wherein the first halogenating agent is chlorine.

10e. The process of any one of the preceding clauses wherein the second halogenating agent is sodium hypochlorite.

11. The process of any one of the preceding clauses wherein step (c) is conducted at a temperature of about 0° C. to about 50° C.

11a. The process of any one of the preceding clauses wherein step (c) conducted at a temperature of about 10° C. to about 30° C.

11b. The process of any one of clauses 1 to 10e wherein step (c) conducted at a temperature of about 20° C. to about 80° C.

11c. The process of any one of clauses 1 to 10e wherein step (c) conducted at a temperature of about 55° C. to about 75° C.

12. The process of any one of the preceding clauses further comprising the step of isolating the compound of formula (A) by co-distillation with water vapor.

13. The process of any one of the preceding clauses further comprising the step of extracting the compound of formula (A) with a water immiscible solvent.

14. The process of any one of the preceding clauses wherein the iron salt in step (c) is ferric chloride, the hydrohalic acid is hydrochloric acid and the ferric chloride is formed by adding ferric oxide to the second liquid mixture.

In any of the processes described herein, ferric chloride containing mixtures can be formed by adding ferric oxide to a mixture comprising hydrochloric acid.

Examples of embodiments in accordance with the invention described herein may include one or more of the following features or combinations thereof.

In another illustrative embodiment, a process for the manufacture of 2,3-dichloropyridine including one or more of the steps shown in Scheme 1 is described.

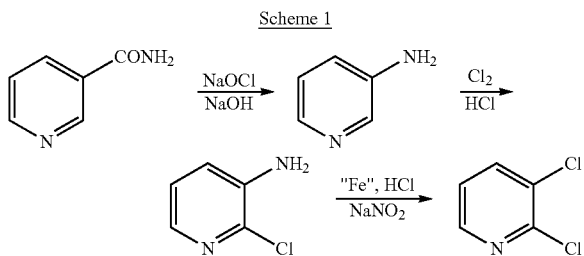

Scheme 1

In another illustrative embodiment, a process for the manufacture of a 2,3-halopyridine including one or more of the steps shown in Scheme 2 is described.

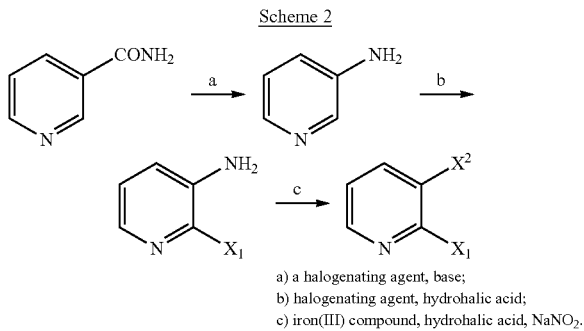

Scheme 2 a) a halogenating agent, base;
b) halogenating agent, hydrohalic acid;
c) iron(III) compound, hydrohalic acid, $NaNO_2$.

Illustratively, niacinamide is a readily available and cost effective precursor to prepare 3-aminopyridine. Conversion of niacinamide to 3-aminopyridine can be achieved in the presence of a halogenating agent and a strong base. Illustrative halogenating agents include, but are not limited to, chlorine, bromine, hypochlorous acid, hypobromous acid, alkali metal (such as lithium, sodium or potassium) hypochlorite, alkali metal hypobromite, or benzyltrimethyl ammonium tribromide, and the like. Illustrative strong bases include, but are not limited to, an alkali metal hydroxide or an alkali earth metal hydroxide, including but not limited to, lithium hydroxide, potassium hydroxide, sodium hydroxide, calcium hydroxide, magnesium hydroxide, and the like. It is understood that the halogenating agent can be added to a mixture of the nicotinamide and the base or the halogenating agent and the base can be added to the nicotinamide concurrently.

Illustratively, 3-amino-2-halopyridines can be prepared by treating a 3-aminopyridine with a halogenating agent in the presence of an acid. Optionally, an iron salt (e.g. an Fe(II) or Fe(III) halide) may also present. Illustrative halogenating agents include, but are not limited to, chlorine, bromine, hypochlorous acid, hypobromous acid, alkali metal (such as lithium, sodium or potassium) hypochlorite, N-chlorosuccinimide, alkali metal hypobromite, N-bromosuccinimide, or benzyltrimethyl ammonium tribromide, and the like Illustrative iron salts useful in the processes described herein include ferric chloride, ferric nitrate, ferric sulfate, ferrous chloride, ferrous nitrate, and ferrous sulfate, and the like.

Illustrative iron (III) compounds useful in the processes described herein include ferric oxide, ferric halides, ferric nitrate, ferric sulfate, and ferric oxychlorides, and the like.

Illustrative hydrohalic acids are hydrochloric acid, hydrobromic acid, hydrofluoric acid and hydroiodic acid.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

The term "optionally substituted" as used herein includes the replacement of hydrogen atoms with other functional groups on the radical that is optionally substituted. Such other functional groups illustratively include, but are not limited to, hydroxyl, halo, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of hydroxyl, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, hydroxy, halo, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of hydroxy, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein the term "liquid mixture" includes homogeneous solutions, liquid slurries, suspensions of one or more solids in a fluid, suspensions of two or more immiscible fluids, and the like. In another embodiment, the compounds described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

EXAMPLES

Example 1

Preparation of 2,3-dichloropyridine from 3-aminopyridine using ferric chloride. To a mixture of 3-aminopyridine (7-5.3 g, 0.800 mole), 32% hydrochloric acid (503.9 g, 4.421 mole), and 40% aqueous ferric chloride (4.5 g, 0.011 mole) mixture was added chlorine (67.6 g, 0.953 mole) keeping the reaction temperature below 25° C. to make the 2-chloro-3-aminopyridine. To this solution was added 40% aqueous ferric chloride (317.0 g, 0.782 mole) and water (100 g) followed by a slow addition of 40% aqueous sodium nitrite (151.0 g, 0.875 mole) keeping the reaction temperature below 30° C. during which time nitrogen gas is evolved. This reaction mixture is worked up using standard work rip procedures to get the final product 2,3-dichloropyridine (83.3 g, 0.563 mole; yield 70%).

Example 2

Preparation of 2,3-dichloropyridine from niacinamide. To a cold mixed solution of 8.8% bleach (1005 g, 1.306 mole) and 50% sodium hydroxide (210 g; 2.625 mole) was added a solution of niacinamide (159 g, 0.302 mole) in eater (254 g) keeping the reaction temperature below 10° C. This reaction mixture was carefully heated to 80° C. and kept between 85-95° C. for two hours. The reaction mixture containing the crude product 3-aminopyridine (114.7 g, 1.219 mole) is used in the EXAMPLE 3 and COMPARATIVE EXAMPLE 1.

Example 3

To the crude 3-aminopyridine (36.6 g, 0.389 mole) from EXAMPLE 2 32% hydrochloric acid (380 g, 3.348 mole) and 40% aqueous ferric chloride (2.2 g, 0.005 mole) was added carefully. To this mixture was added chlorine (33.2 g, 0.468 mole) keeping the reaction temperature below 25° C. to make the 2-chloro-3-aminopyridine. To this solution was added 40% aqueous ferric chloride (157.8 g, 0.389 mole) followed by a slow addition of 40% aqueous sodium nitrite (75.4 g, 0.435 mole) keeping the reaction temperature below 30° C. during which time nitrogen gas is evolved. This reaction mixture is worked up using standard work up procedures to get the final product 2,3-dichloropyridine (24.9 g, 0.168 mole; yield 43%).

Example 4

Preparation of 2,3-Dichloropyridine Using Iron (III) Oxide

1 Equivalent of Fe to 3-Amino-2-Chloropyridine: A three liter, three necked flask was equipped with a mechanical stirrer, a thermocouple connected to a temperature controller, a heating mantle, and a condenser vented to a water-filled bubbler. The flask was charged with CLAMP mixture (1009.0 g, 1.) and iron (III) oxide (110.0 g, 1.378 mole-equivalents of Fe). The reaction mixture was heated to 66° C., and a 40% solution of sodium nitrite (266.0 g, 1.542 mole) was added to the flask via a syringe pump at 65-75° C. over a 3.65-hour period. The reaction mixture was then stirred for 31 minutes without additional heating. 50% sodium hydroxide solution (450.0 g, 5.625 mole) was added via a syringe pump at 50-75° C. over a 3.25-hour period, resulting in a pH of 5.9. The pH was further adjusted to 9.0 using 50% sodium hydroxide solution (17.0 g, 0.213 mole). The reaction mixture was stirred overnight, resulting in a final pH of 8.9. The reaction mixture was heated to reflux, and the 2,3-dichloropyridine was isolated via steam distillation. The crude weight yield was 188.5 g. GC analysis of the crude product was 87.22%. Chemical yield=188.5×0.8722=164.4 g. The procedure above was repeated with different ratios of iron (III) oxide, yielding the results shown in Table 1.

The CLAMP mixture used was prepared by chlorination of 3-aminopyridine in a large scale version of the first step of EXAMPLE 1. To a mixture of 948 Kg of 3-aminopyridine, 5300 Kg 32% hydrochloric acid, and 217 Kg of 40% aqueous ferric chloride was added 895 Kg of chlorine at a rate that allowed the temperature of the reaction mixture to be maintained between 20-35° C.

TABLE 1

| ID | $Fe_2O_3$ (mol eq. Fe) | Yield | Wt % 3CP | Wt % 23DCP | Wt % 236TCP** | Wt % 3A2CP |
|---|---|---|---|---|---|---|
| 1 | 1.0 | 188.5 | 2.11 | 87.22 | 8.84 | 0.06 |
| 2 | 0.7 | 188.5 | 2.15 | 87.81 | 8.66 | 0.02 |
| 3 | 0.5 | 184.5 | 2.20 | 87.73 | 8.74 | 0.03 |
| 4 | 0.3 | 172.1 | 2.18 | 87.35 | 8.95 | 0.01 |
| 5 | 0.1 | 134.1 | 2.37 | 86.26 | 9.37 | 0.01 |
| 6* | 1.0 (CuO) | 181.2 | 2.93 | 86.33 | 9.23 | 0.01 |

TABLE 1-continued

| ID | Wt % 234TCP** | Wt % 2346TCP** |
|---|---|---|
| 1 | 0.48 | 0.30 |
| 2 | 0.59 | 0.32 |
| 3 | 0.60 | 0.32 |
| 4 | 0.64 | 0.33 |
| 5 | 0.77 | 0.36 |
|   | 0.53 | 0.24 |

*comparative example, no Fe$_2$O$_3$ added. 3CP = 3-chloropyridine; 23DCP = 2,3- dichloropyridine; 26DCP = 2,6-dichloropyridine; 3A2CP = 3-amino-2-chloropyridine; 234TCP = 2,3,4-trichloropyridine; 236TCP = 2,3,6,-trichloropyridine; 2346TCP = 2,3,4,6-tetrachloropyridine
**Primarily from over chlorination in the conversion of 3-aminopyridine to 3-amino-2-chloropyridine Comparative Example 1A Preparation of 2,3-Dichloropyridine Using Copper(II) Oxide 1 Equivalent of Cu to 3-Amino-2-Chloropyridine: A three liter, three necked flask was equipped with a mechanical stirrer, a thermocouple connected to a temperature controller, a heating mantle, and a condenser vented to a water-filled bubbler. The flask was charged with CLAMP mixture (1009.0 g) and copper (II) oxide (109.6 g, 1.378 mole). The reaction mixture was heated to 66° C., and a 40% solution of sodium nitrite (266.0 g, 1.542 mole) was added to the flask via a syringe pump at 65-75° C. over a 3.68-hour period. The reaction mixture was then stirred for 30 minutes without additional heating. 50% sodium hydroxide solution (450.0 g, 5.625 mole) was added via a syringe pump at 50-75° C. over a 3.07-hour period, resulting in a pH of 12.4. The reaction mixture was stirred overnight, resulting in a final pH of 10.9. The pH was further adjusted to 9.5 using 37% hydrochloric acid solution (6.0 g, 0.061 mole). The reaction mixture was heated to reflux, and the 2,3-dichloropyridine was isolated via steam distillation. The crude weight yield was 181.2 g. GC analysis of the crude product was 86.33%. Chemical yield=181.2×0.8633=156.4 g.

Comparative Example 1

Preparation of 2,3-dichloropyridine from 3-aminopyridine using cupric chloride. To a mixture of 3-aminopyridine (50.0 g, 0.531 mole), 36% hydrochloric acid (201.5 g, 1.989 mole), and 40% aqueous ferric chloride (3.1 g, 0.008 mole) mixture was added chlorine (44.0 g, 0.621 mole) keeping the reaction temperature below 25° C. to make the 2-chloro-3-aminopyridine. To this solution was added cupric oxide (42.3 g, 0.532 mole) and 36% hydrochloric acid (94.6 g, 0.934 mole) followed by a slow addition of 40% aqueous sodium nitrite (102.9 g, 0.596 mole) keeping the reaction: temperature below 30° C. during which time nitrogen gas is evolved. This reaction mixture is worked up using standard work up procedures to get the final product 2,3-dichloropyridine (59.7 g, 0.404 mole; yield 76%).

Comparative Example 2

To the crude 3-aminopyridine (34.3 g, 0.364 mole) from EXAMPLE 2 32% hydrochloric acid (358 g, 3.141 mole) and 40% aqueous ferric chloride (2.1 g, 0.005 mole) was added carefully and to this mixture was added chlorine (31.7 g, 0.447 mole) keeping the reaction temperature below 25° C. to make the 2-chloro-3-aminopyridine. To this solution was added cupric oxide (28.6 g, 0.360 mole) followed by a slow addition of 40% aqueous sodium nitrite (69.5 g, 0.403 mole) keeping the reaction temperature below 30° C. during which time nitrogen gas is evolved. This reaction mixture is worked up using standard work up procedures to get the final product 2,3-dichloropyridine (29.6 g, 0.200 mole; yield 55%).

While certain embodiments of the present invention have been described and/or exemplified above, it is contemplated that considerable variation and modification thereof are possible. Accordingly, the present invention is not limited to the particular embodiments described and/or exemplified herein.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

What is claimed is:

1. A process for the manufacture of a compound of formula (A)

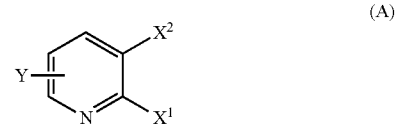

(A)

wherein

X$^1$ and X$^2$ are in each instance independently selected from the group consisting of Cl and Br;

Y represents from 0 to 3 substituents independently selected in each instance from the group consisting of halide, CN, NO$_2$, OH, optionally substituted alkyl, optionally substituted aryl, and optionally substituted heteroaryl; and wherein the process comprises the step (c) of adding a first liquid mixture comprising a metal nitrite salt to a second liquid mixture comprising a compound of formula (B)

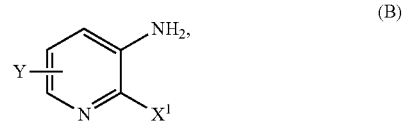

(B)

a hydrohalic acid, and an iron compound, wherein the iron compound is an iron(III) compound, or ferrous chloride, or ferrous nitrate, or ferrous sulfate.

2. The process of claim 1 wherein the iron (III) compound is an iron salt.

3. The process of claim 1 further comprising the step (b) of reacting a compound of formula (C)

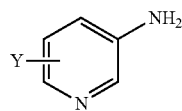

with a first halogenating agent in the presence a hydrohalic acid to give the compound of formula (B).

4. The process of claim 1 further comprising the step (a) of reacting a compound of formula (D)

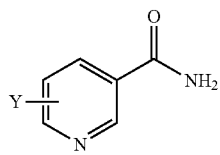

with a base and a second halogenating agent to give the compound of formula (C).

5. The process of claim 3 wherein steps (b) and (c) are conducted in the same reaction vessel.

6. The process of claim 4 wherein steps (a), (b), and (c) are conducted in the same reaction vessel.

7. The process of claim 4 wherein the second halogenating agent is selected from the group consisting of group consisting of chlorine, N-chlorosuccinimide, bromine, N-bromosuccinimide, hypochlorous acid, hypobromous acid, alkali metal hypochlorites, alkali metal hypobromites, and benzyltrimethyl ammonium tribromide.

8. The process of claim 3 wherein the first halogenating agent is selected from the group consisting of bromine, N-bromosuccinimide, chlorine, N-chlorosuccinimide, hydrochloric acid and hydrogen peroxide, hypochlorous acid, hypobromous acid, alkali metal hypochlorites, alkali metal hypobromites, and benzyltrimethyl ammonium tribromide.

9. The process of claim 1 wherein Y is not present.

10. The process of claim 1 wherein $X^1$ is chloro.

11. The process of claim 1 wherein $X^2$ is chloro.

12. The process of claim 1 wherein Y is absent; and $X^1$ and $X^2$ are both chloro.

13. The process of claim 1 wherein the iron compound is selected from the group consisting of ferric chloride, ferric nitrate, ferric sulfate, ferrous chloride, ferrous nitrate, and ferrous sulfate.

14. The process of claim 2 wherein the iron salt is ferric chloride.

15. The process of claim 1 wherein the hydrohalic acid is hydrochloric acid.

16. The process of claim 3 wherein the first halogenating agent is chlorine.

17. The process of claim 4 wherein the second halogenating agent is sodium hypochlorite.

18. The process of claim 1 wherein step (c) conducted at a temperature of about 20° C. to about 80° C.

19. The process of claim 1 wherein step (c) conducted at a temperature of about 55° C. to about 75° C.

20. The process of claim 1 further comprising the step of isolating the compound of formula (A) by co-distillation with water vapor.

21. The process of claim 1 further comprising the step of extracting the compound of formula (A) with a water immiscible solvent.

22. The process of claim 1 wherein the iron (III) compound in step (c) is ferric chloride, the hydrohalic acid is hydrochloric acid, and the ferric chloride is formed by adding ferric oxide to the second liquid mixture.

* * * * *